June 19, 1973 H. KERRIGAN Plant Pat. 3,362
AZALEA PLANT
Filed Oct. 18, 1971
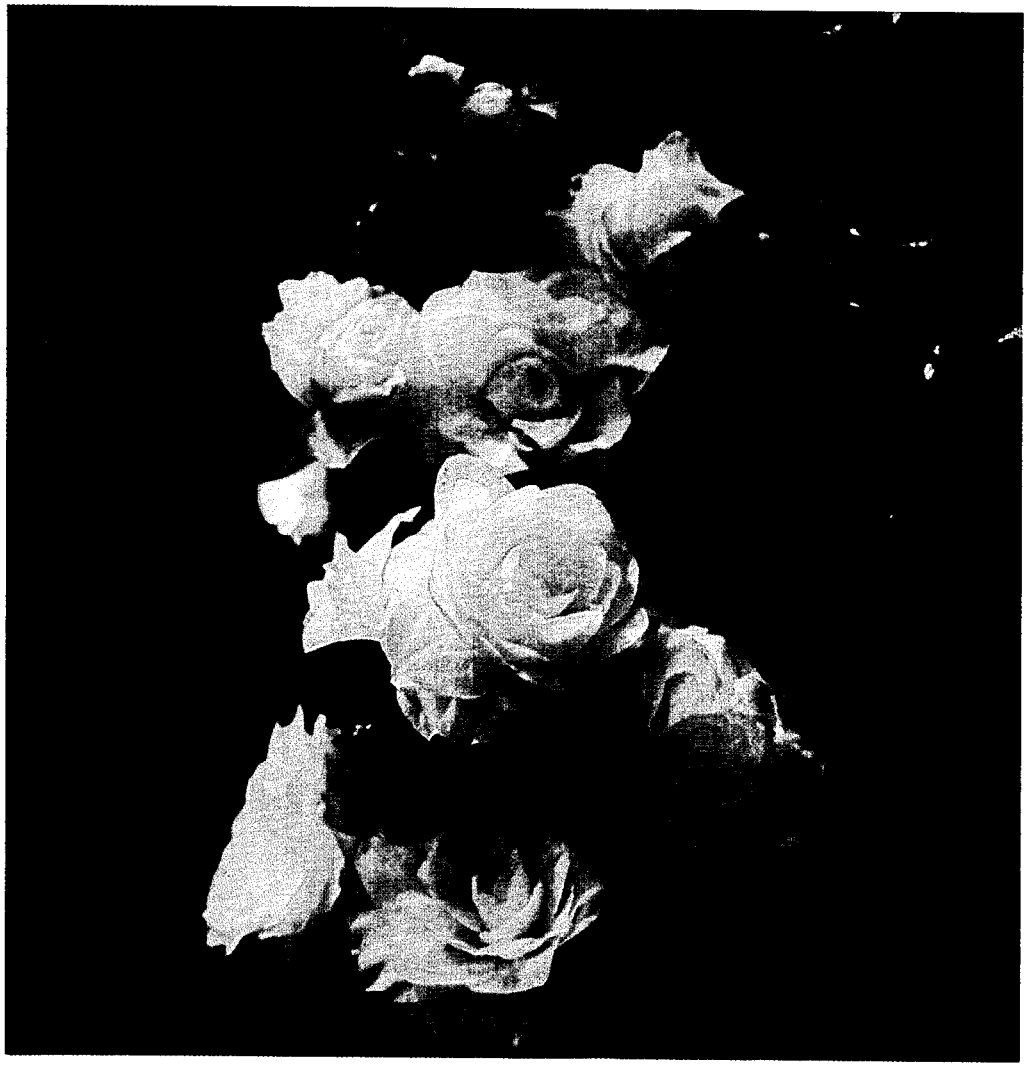

United States Patent Office

Plant Pat. 3,362
Patented June 19, 1973

3,362

AZALEA PLANT

Howard Kerrigan, 25783 Mission Blvd., Hayward, Calif.

Filed Oct. 18, 1971, Ser. No. 190,240
Int. Cl. A01h *7/00*
U.S. Cl. Plt.—55 1 Claim

The invention relates to a new and distinct variety of azalea plant of the Belgian Indica type, originated by me in 1956 as a consequence of a breeding program begun in 1943. The parentage of my new azalea plant is as follows: Blushing Bride (unpatented) the seed parent × Gables Rosebud(unpatented) the pollen parent.

The object of the cross was to produce a late flowering plant with more vigor and more double bloom than Blushing Bride and larger flowers than Rosebud. These objectives were achieved along with other desirable improvements, as evidenced by the following unique combination of characteristics which are outstanding in the new variety and which distinguish it from its parents as well as from all other varieties of which I am aware. My new variety is primarily characterized by: abundant, long lived, dark green foliage; fully double, pure white buds and blooms with buds of classical rosebud form, borne on a vigorous well-branched plant which flowers profusely over a long period and which retains its peak bloom for an exceptionally long period of time, which results in an unusually long marketability period.

Asexual reproduction of my new variety by cuttings, through a series of annual propagations at Oakland and Hayward, Calif, in 1959–1969 shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of one, two, and three year old flowering plants at Hayward, Oakland and Santa Rosa, Calif.

In overall habit and appearance this variety is similar to "Cloud Nine" (plant patent applied for) but differs from that variety in that:

The plant is more upright, rounded and heavily branched.

The foliage is darker, glossier, especially below, and the young strigae more colorless and hyaline.

The flowers are frequently in threes, often, twos and rarely ones; they are more yellow. They are smaller; 1¾–2″ across.

The peduncle is longer and more slender and with much less strigae, (½–7/16″ long x 1/16–6/64″ across).

The calyx is more petalaceous and larger (1″ across and ½–⅝″ deep) with the lobes flaring.

The margins of the lobes are ciliate and irregularly serrate, and the throat is less green.

The staminodia are variously fused and incised and the number ranges from 8–12.

The pistils are deformed, small, green, pubescent at base (at least in part) ⅜–½″ long with both styles and stigmas deformed and papillate.

Having thus disclosed my invention, I claim:

1. A new and distinct variety of azalea plant of the Belgian Indica type substantially as herein shown and described primarily characterized by: abundant, long lived, dark green foliage; fully double pure white buds and blooms with buds of classical rosebud form, borne on a vigorous, well-branched plant which flowers profusely over a long period and which retains its peak bloom for an exceptionally long period of time, which results in an unusually long marketability period.

No references cited.

ROBERT E. BAGWILL, Primary Examiner